US012728143B2

(12) United States Patent
Higurashi et al.

(10) Patent No.: US 12,728,143 B2
(45) Date of Patent: Sep. 8, 2026

(54) METHOD AND COMPOSITION FOR MAINTENANCE AND/OR IMPROVEMENT OF MEMORY/LEARNING ABILITY

(71) Applicant: MEGMILK SNOW BRAND Co., Ltd., Hokkaido (JP)

(72) Inventors: Satoshi Higurashi, Hokkaido (JP); Kentaro Noma, Aichi (JP); Ikue Mori, Aichi (JP); Shunji Nakano, Aichi (JP); Yuki Tsukada, Aichi (JP)

(73) Assignee: MEGMILK SNOW BRAND CO., LTD., Hokkaido (JP)

( * ) Notice: Subject to any disclaimer, the term of this patent is extended or adjusted under 35 U.S.C. 154(b) by 543 days.

(21) Appl. No.: 17/628,744

(22) PCT Filed: Jul. 27, 2020

(86) PCT No.: PCT/JP2020/028686
§ 371 (c)(1),
(2) Date: Jan. 20, 2022

(87) PCT Pub. No.: WO2021/015288
PCT Pub. Date: Jan. 28, 2021

(65) Prior Publication Data

US 2022/0265737 A1 Aug. 25, 2022

(30) Foreign Application Priority Data

Jul. 24, 2019 (JP) ................................ 2019-136268

(51) Int. Cl.

| | |
|---|---|
| ***A61K 39/02*** | (2006.01) |
| ***A23C 9/123*** | (2006.01) |
| ***A23K 10/18*** | (2016.01) |
| ***A23L 2/52*** | (2006.01) |
| ***A23L 33/00*** | (2016.01) |
| ***A23L 33/135*** | (2016.01) |
| ***A61K 9/00*** | (2006.01) |
| ***A61K 35/742*** | (2015.01) |
| ***A61K 35/744*** | (2015.01) |
| ***A61K 35/747*** | (2015.01) |
| ***A61K 47/36*** | (2006.01) |
| ***A61K 47/44*** | (2017.01) |
| ***A61K 47/46*** | (2006.01) |
| ***A61P 25/28*** | (2006.01) |

(52) U.S. Cl.
CPC ........... *A61K 35/747* (2013.01); *A23C 9/123* (2013.01); *A23K 10/18* (2016.05); *A23L 2/52* (2013.01); *A23L 33/135* (2016.08); *A23L 33/40* (2016.08); *A61K 9/0056* (2013.01); *A61K 35/742* (2013.01); *A61K 35/744* (2013.01); *A61K 47/36* (2013.01); *A61K 47/44* (2013.01); *A61K 47/46* (2013.01); *A61P 25/28* (2018.01); *A23V 2002/00* (2013.01); *A23V 2400/11* (2023.08)

(58) Field of Classification Search
None
See application file for complete search history.

(56) References Cited

U.S. PATENT DOCUMENTS

| | | | |
|---|---|---|---|
| 6,284,243 B1 * | 9/2001 | Masuyama ............ | A61P 25/28 424/195.16 |
| 8,343,482 B2 | 1/2013 | Bergonzelli et al. | |
| 2011/0280837 A1 | 11/2011 | Bergonzelli et al. | |
| 2012/0328735 A1 | 12/2012 | Uchida et al. | |
| 2014/0363410 A1 | 12/2014 | Bergonzelli Degonda et al. | |
| 2018/0355445 A1 | 12/2018 | Kim et al. | |
| 2019/0030097 A1 | 1/2019 | Kim et al. | |

FOREIGN PATENT DOCUMENTS

| | | |
|---|---|---|
| CN | 107455698 | 12/2017 |
| CN | 108541951 | 9/2018 |
| EP | 2 735 616 | 5/2014 |
| EP | 3677127 A1 | 8/2018 |
| JP | 9-23848 | 1/1997 |
| JP | H09-191872 A | 7/1997 |
| JP | 2009-242431 A | 10/2009 |

(Continued)

OTHER PUBLICATIONS

Boseley, S. (The Guardian. Jan. 5, 2012, pp. 1-3).*
Gareau et al (Gut microbiota. 2011, 60: 307-317).*
Office Action dated Mar. 24, 2025, issued in Thailand patent application No. 2201000326, with English translation thereof.*
Office Action issued Oct. 20, 2023 in Indonesian patent application No. P00202200416, with English translation thereof.
Fujiwara et al., "Proteinaceous Factor(s) in Culture Supernatant Fluids of Bifidobacteria Which Prevents the Binding of Enterotoxigenic *Escherichia coli* to Gangliotetraosylceramide," *Applied Environmental Microbiology,* Feb. 1997, p. 506-512.
Extended European Search Report issued Jul. 14, 2023 in European patent application No. 20843402.7.

(Continued)

*Primary Examiner* — Jennifer E Graser
(74) *Attorney, Agent, or Firm* — Greenblum & Bernstein, P.L.C.

(57) ABSTRACT

A medicine, a food or a drink and feed which are effective for preventing and/or improving decline, occurring with age (senescence), in memory and learning ability are provided. A novel microorganism having the effect of preventing and/or improving decline, occurring with age (senescence,) in memory and learning ability is provided. More specifically, the microorganism is characterized by being a microorganism belonging to *Lactobacillus, Bifidobacterium, Streptococcus, Leuconostoc* or *Pediococcus*, more specifically a microorganism belonging to any of *Lactobacillus acidophilus, Lactobacillus gasseri, Lactobacillus gallinarum, Lactobacillus johnsonii, Lactobacillus delbrueckii* subsp. *delbrueckii, Bifidobacterium catenulatum, Bifidobacterium pseudolongum, Bifidobacterium bifidum, Bifidobacterium breve, Bifidobacterium longum, Streptococcus thermophiles, Leuconostoc mesenteroides* subsp. *dextranicum, Leuconostoc lactis, Pediococcus acidilactici* and *Pediococcus pentosaceus.*

8 Claims, 2 Drawing Sheets

(56) References Cited

FOREIGN PATENT DOCUMENTS

| | | | |
|---|---|---|---|
| JP | 5155960 | | 12/2012 |
| JP | 5155961 | | 12/2012 |
| JP | 2013-5757 | | 1/2013 |
| JP | 2013-184956 | | 9/2013 |
| JP | 2015-503913 | | 2/2015 |
| JP | 2015-47121 | | 3/2015 |
| JP | 2017-160200 | A | 9/2017 |
| JP | 2017-197486 | | 11/2017 |
| JP | 2017-222601 | | 12/2017 |
| JP | 2018-531595 | | 11/2018 |
| KR | 10-2011-0057550 | | 6/2011 |
| KR | 10-2019-0000450 | | 1/2019 |
| WO | 2018/143793 | | 8/2018 |
| WO | 2019/044960 | A1 | 3/2019 |

OTHER PUBLICATIONS

Office Action issued May 10, 2023 in Japanese application No. 2019-203210, with English machine translation thereof.
Office Action issued Feb. 23, 2024 issued in Chinese patent application No. 202080066097.X, with English machine translation thereof.
Office Action issued Mar. 6, 2024, issued in Japanese patent application No. 2019-203210, with English machine translation thereof.
Office Action issued Mar. 13, 2024, issued in Taiwanese patent application No. 109124881, with English machine translation thereof.
Allen, A. P. et al., "*Bifidobacterium longum* 1714 as a translational psychobiotic: modulation of stress, electrophysiology and neurocognition in healthy volunteers", Transl. Psychiatry, 2016, vol. 6, No. e939, pp. 1-7, doi: 10.1038/tp.2016.191.
O'Hagan, C. et al., "Long-term multi-species Lactobacillus and Bifidobacterium dietary supplement enhances memory and changes regional brain metabolites in middle-age rats", Neurobiology of Learning and Memory, 2017, vol. 144, pp. 36-47, http://dx.doi.org/10.1016/j.nlm.2017.05.015.
Parois, S et al., "The influcence of a probiotic supplementation on memory in quail suggests a role of gut microbiota on cognitive abilities in birds", Behavioural Brain Research, 2017, vol. 331, pp. 47-53, http://dx.doi.org/10.1016/j.bbr.2017.05.022.
Ni, Y. et al., "*Lactobacillus* and *Bifidobacterium* improves physiological function and cognitive ability in aged mice by the regulation of gut microbiota", Mol. Nutr. Food Res., Sep. 25, 2019, vol. 63, No. 22, 1900603, pp. 1-14, DOI:10.1002/mnfr.201900603.
Nagasaki, Y. et al., "Effect of a dietary supplement containing heat-killed Bifidobacterium longum N61 on neurocognitive fuctions in healthy old adults with perceived memory impairment—A Randomized, Double-blind, Placebo-controlled Trial—", Jpn. Pharmacol. Ther., 2019, vol. 47, No. 10, pp. 1677-1688.
Lee, H.-J. et al., "*Lactobacillus johnsonii* CJLJ103 attenuates scopolamine-induced memory impairment in mice by increasing BDNF expression and inhibiting NF-κB activation", J. Microbiol. Biotechnol., 2018, vol. 28, No. 9, pp. 1443-1446, https://doi.org/10.4014/jmb.1805.05025.
International Search Report issued in PCT/JP2020/028686, dated Sep. 8, 2020.
International Preliminary Report on Patentability issued in PCT/JP2020/028686 on Jan. 25, 2022.
Decision of Refusal issued Sep. 30, 2023 in Japanese patent application No. 2019-203210, with English translation thereof.
Decision of Refusal issued Nov. 18, 2024 in Taiwanese patent application No. 109124881, with English translation thereof.
Office Action dated Sep. 13, 2024, issued in Chinese patent application No. 202080066097.X, with English machine translation thereof.
Office Action dated Feb. 12, 2025, issued in Japanese patent application No. 2023-213602, with English machine translation thereof.
Office Action dated Feb. 11, 2025 in Chinese patent application No. 202080066097.X, with English translation thereof.
Notification of Reexamination issued Jul. 4, 2025 in Chinese patent application No. 202080066097.X and English.
Office Action dated Jul. 25, 2025, issued in Australian patent application No. 2020318631.
Decision of Refusal dated Jun. 1, 2025, issued in Japanese patent application No. 2023-213602, with English machine translation thereof.
Reexamination Decision dated Oct. 23, 2205, issued in Chinese patent application No. 202080066097.X, with English machine translation thereof.
Office Action dated Dec. 12, 2025, issued in Australian patent application No. 2020318631.
Office Action dated Nov. 26, 2025, issued in Canadian patent application No. 3,147,743.
Office Action dated Dec. 19, 2025, issued in Korean patent application No. 10-2022-7005759, with English machine translation thereof.
Office Action issued Apr. 13, 2026 in New Zealand patent application No. 785452.
Office Action issued Mar. 25, 2026 in Taiwanese patent application No. 109124881, with English machine translation thereof.
Office Action issued Mar. 3, 2025 in Taiwanese patent application No. 109124881, with English machine translation thereof.

* cited by examiner

[FIG. 1]
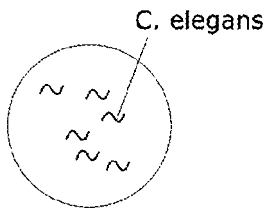
cultivation with food(OP50 or Lactic acid bacteria) at 23℃
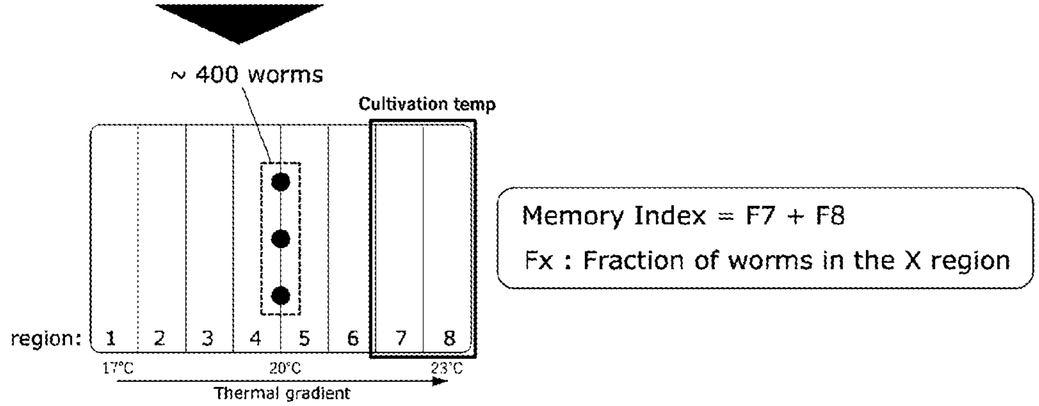

[FIG. 2]
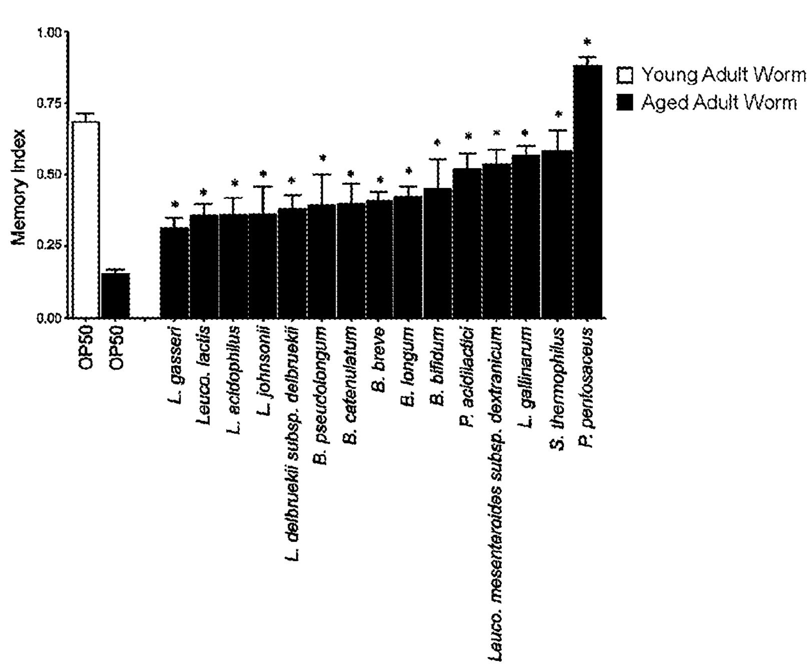
(Dunnett's Test, *: P<0.05, Showing Presence or Absence of Significant Difference from Results of Aged Adult Worms Which Have Taken OP50)

METHOD AND COMPOSITION FOR MAINTENANCE AND/OR IMPROVEMENT OF MEMORY/LEARNING ABILITY

TECHNICAL FIELD

The present invention relates to an agent for preventing or improving decline, occurring with age (senescence), in memory and learning ability and/or a food or a drink having the effect of preventing or improving decline, occurring with age (senescence), in memory and learning ability.

BACKGROUND ART

In Japan, the percentage of the elderly population of the age of 65 years or older has exceeded 21% of the entire population in 2010, and the country has entered a super-aged society. The percentage of the elderly people is expected to increase continuously and is said to reach 40% by 2060. Under the circumstances, solving the problems of the increasing elderly population such as problems of the health care and the welfare is an urgent issue.

With the increase in the elderly population, an increase in cognitive impairment such as decline in memory and learning ability and dementia in the middle to upper age group has become a problem. It is generally believed that the microstructure of neurons in the brain changes with age and that, through deposition of abnormal protein and cell loss, the brain shrinks, which leads to a decline in the cognitive function. The state in which the cognitive function has declined to a pathological condition due to cerebral infarction, cerebral hemorrhage, excessive accumulation of abnormal protein or the like in addition to the age-related changes is dementia.

As of 2012, about 4.62 million people, which is 15%, of the elderly people of the age of 65 years or older are estimated to have dementia, and there are about 4 million mild cognitive impairment patients who are called possible dementia. Japan at the moment is said to undergo "an era of 8 million dementia patients".

Although therapeutic agents for dementia have been developed, the therapeutic agents at the moment are used for the purpose of delaying the progress, and fundamental treatment has not been achieved. For healthy elderly people or elderly people with mild cognitive impairment who are positioned as the state of pre-dementia, it has been suggested that decline in cognitive function such as memory and learning ability may be prevented or improved and that the risk of the onset of dementia may be even decreased through appropriate intervention such as a change of the dietary habit or exercise (Psychiatria et Neurologia Japonica 111, 26-30, (2009)). Therefore, foods and drinks which can be continuously taken in the daily life and which are highly safe and side-effect free have drawn attention.

Microorganisms used for foods such as lactic acid bacteria are widely used for fermented foods such as cheese, yogurt and pickles, lactic acid bacteria beverage and the like and have been produced worldwide for a long time in a large amount due to the relatively low cost of supply and the high palatability. Recently, the microorganisms have drawn attention as health foods also having health effects which are preferable for the health, such as intestinal regulation effect including prevention of constipation and improvement of diarrhea, prevention of an infection and immunostimulation effect. Regarding the relevance to aging or cognitive function, for example, it has been disclosed that *Lactobacillus gasseri* and *Bifidobacterium longum* are effective for age-related metabolic abnormality (U.S. Pat. Nos. 5,155,961 and 5,155,960) and that *Lactobacillus reuteri* strain DSM 17938 is effective for the development of cognitive function of juvenile mammals (JP-T-2015-503913, the term "JP-T" as used herein means a published Japanese translation of a PCT patent application).

The effects of the microorganisms on decline in memory and learning ability occurring with age (senescence), however, have not been elucidated.

Nematode *Caenorhabditis elegans* (called *C. elegans* below) can sense various external stimuli and conduct various responses using a simple neural circuit composed of 302 neurons. Because *C. elegans* memorize the ambient temperature in association with its past cultivation conditions as the comfortable temperature, they migrate to and move isothermally around that temperature on a temperature gradient. For example, when *C. elegans* which has been cultured at 23° C. is placed on a temperature gradient of 17° C. to 23° C. without any food, the *C. elegans* migrates to around 23° C. Moreover, when the cultivation temperature is shifted from 23° C. to 17° C., the worm, which had acquired memory of 23° C., acquires memory of the new temperature, 17° C., in about four hours and migrates to around 17° C. in a temperature gradient (Proc. Natl. Acad. Sci. USA, 72, 4061-4065 (1975); Genetics, 169, 1437-1450 (2005); J. Neurosci. Methods, 154, 45-52 (2006)). This behavior is called thermotaxis and is known as an excellent model system reflecting the plasticity of neural functions such as memory and learning (Curr. Opin. Neurobiol., 17, 712-719 (2007)).

In an experiment of killing each neuron with laser which has been conducted by the inventors, the neurons critical for the thermotaxis behavior have been identified, and it is known that the thermotaxis behavior is based on a very simple neural circuit (Nature, 376, 344-348 (1995)). Moreover, a research group of the inventors has analyzed the process of the formation of thermal memory through a genome-wide microarray analysis, a molecular genetic method and an imaging technique. As a result, it has been found that *C. elegans* perceives the ambient temperature with the whole body through HSF-1, which is a transcription factor, when *C. elegans* memorizes the cultivation temperature. Moreover, it has been shown that the temperature perception causes a change in gene expression and that, as a result, the thermal signals are accumulated as memory in AFD neuron, which is thermosensory neuron in the neural circuit, via a female hormone estrogen (Nat. Neurosci., 14, 984-92 (2011)).

Furthermore, as a result of search for cells in which the *C. elegans* ortholog of CREB, a representative transcription factor responsible for memory, functions, the inventors have found that CREB ortholog functions only in AFD neuron (EMBO Rep., 12, 855-862 (2011)). This suggests that, of all the neurons of *C. elegans*, AFD neuron is the only neuron having thermal memory through CREB. These studies have elucidated a part of the molecular mechanism for the formation of thermal memory.

Although nematodes is the organism that is phylogenetically very distant from mammals from an evolutionary viewpoint, the molecular mechanisms at the cell level have a lot in common. It has been reported that molecules which are known to be relevant to memory in mammals also involve in thermotaxis in nematodes. For example, there are many reports: CREB (CRH-1 in nematodes), which is a factor related to memory in mammals, involves in acquisition of thermal memory in nematodes (EMBO Rep., 12, 855-862 (2011)); serotonin, which is an intracerebral transmitter related to memory in mammals, regulates thermotaxis in nematodes (PLoS One., 8, 1-10 (2013)); calcineurin (RCAN-1 in nematodes), which is a factor related to memory in mammals, relates to thermotaxis behavior in nematodes (J. Mol. Biol., 427, 3457-3468 (2015)); and the like.

Furthermore, cases have been reported in which a component which has been observed to be effective for the nervous system in nematodes exhibits an effect on the brain-nervous system also in mammals. That is, for example, it has been reported that orally taken α-lipoic acid improves age-related decline in associative learning behavior in nematodes and mammals (Neurobiol. Aging., 26, 899-905 (2005); J. Med. Food., 15, 713-7 (2012)) and that orally taken curcumin improves age-related cognitive impairment in nematodes and mammals (Neurobiol Aging., 39, 69-81 (2016); Geroscience., 40, 73-95 (2018)).

Therefore, the thermotaxis behavior of *C. elegans* is believed to be a model system suitable for analyzing the molecular mechanisms of temperature perception and memory.

CITATION LIST

Patent Literature

[Patent Document 1] U.S. Pat. No. 5,155,961

[Patent Document 2] U.S. Pat. No. 5,155,960

[Patent Document 3] JP-T-2015-503913

Non Patent Literature

[Non-Patent Document 1] Katsuyoshi Mizukami, Psychiatria et Neurologia Japonica 111, 26-30, (2009)

[Non-Patent Document 2] Hedgecock, E. M. & Russell, R. L.: Normal and mutant thermotaxis in the nematode *Caenorhabditis elegans*. Proc. Natl. Acad. Sci. USA, 72, 4061-4065 (1975)

[Non-Patent Document 3] Mohri, A., Kodama, E., Kimura, K. D. et al.: Genetic control of temperature preference in the nematode *Caenorhabditis elegans*. Genetics, 169, 1437-1450 (2005)

[Non-Patent Document 4] Ito, H., Inada, H. & Mori, I.: Quantitative analysis of thermotaxis in the nematode *Caenorhabditis elegans*. J. Neurosci. Methods, 154, 45-52 (2006)

[Non-Patent Document 5] Mori, I., Sasakura, H. & Kuhara, A.: Worm thermotaxis: a model system for analyzing thermosensation and neural plasticity. Curr. Opin. Neurobiol., 17, 712-719 (2007)

[Non-Patent Document 6] Mori, I. & Ohshima, Y.: Neural regulation of thermotaxis in *Caenorhabditis elegans*. Nature, 376, 344-348 (1995)

[Non-Patent Document 7] Sugi, T., Nishida, Y., & Mori, I.: Regulation of behavioral plasticity by systemic temperature signaling in *Caenorhabditis elegans*. Nat. Neurosci., 14, 984-92 (2011)

[Non-Patent Document 8] Nishida, Y., Sugi, T., Nonomura, M. et al.: Identification of the AFD neuron as the site of action of the CREB protein in *Caenorhabditis elegans* thermotaxis. EMBO Rep., 12, 855-862 (2011)

[Non-Patent Document 9] Li, Y., Zhao, Y., Huang, X., et al.: Serotonin control of thermotaxis memory behavior in nematode *Caenorhabditis elegans*. PLoS One., 8, 1-10 (2013)

[Non-Patent Document 10] Li, W., Bell, H. W, Ahnn, J., Lee, S. K.: Regulator of Calcineurin (RCAN-1) Regulates Thermotaxis Behavior in *Caenorhabditis elegans*. J. Mol. Biol., 427, 3457-3468 (2015)

[Non-Patent Document 11] Murakami, S., Murakami, H.: The effects of aging and oxidative stress on learning behavior in *C. elegans*. Neurobiol. Aging., 26, 899-905 (2005)

[Non-Patent Document 12] Cui, Y., Shu, Y., Zhu, Y., Shi, Y., Le, G.: High-fat diets impair spatial learning of mice in the Y-maze paradigm: ameliorative potential of a-lipoic acid. J. Med. Food., 15, 713-7 (2012)

[Non-Patent Document 13] Miyasaka, T., Xie, C., Yoshimura, S., et al.: Curcumin improves tau-induced neuronal dysfunction of nematodes. Neurobiol. Aging., 39, 69-81 (2016)

[Non-Patent Document 14] Sarker, M. R., Franks, S. F.: Efficacy of curcumin for age-associated cognitive decline: a narrative review of preclinical and clinical studies. Geroscience., 40, 73-95 (2018)

SUMMARY OF INVENTION

Technical Problem

The invention relates to provision of a novel microorganism having the effect of preventing and/or improving decline, occurring with age (senescence), in memory and learning ability.

Solution to Problem

From the viewpoint of preventing or improving various dysfunctions in the living body using food materials which can be taken daily, the present inventors have focused on microorganisms used for foods and components contained therein and have conducted intensive studies to solve the problems. As a result, the inventors have found the effect of preventing and/or improving decline, occurring with age (senescence), in memory and learning ability by cells or a culture of microorganisms of different genera and have thus completed the invention. That is, the invention has the following features.

(1) A composition for maintaining and/or improving memory and learning ability containing cells or a culture of one or more microorganisms belonging to any of *Lactobacillus, Bifidobacterium, Streptococcus, Leuconostoc* and *Pediococcus*.

(2) The composition for maintaining and/or improving memory and learning ability according to (1) which is characterized in that the *Lactobacillus* is one or more selected from *Lactobacillus acidophilus, Lactobacillus gasseri, Lactobacillus gallinarum, Lactobacillus johnsonii* and *Lactobacillus delbrueckii* subsp. *delbrueckii.*

(3) The composition for maintaining and/or improving memory and learning ability according to (1) which is characterized in that the *Lactobacillus* is not one or more selected from *Lactobacillus acidophilus, Lactobacillus gallinarum, Lactobacillus brevis, Lactobacillus casei, Lactobacillus crispatus, Lactobacillus delbrueckii, Lactobacillus delbrueckii* subsp. *delbrueckii, Lactobacillus fermentum, Lactobacillus gasseri, Lactobacillus helveticus, Lactobacillus johnsonii, Lactobacillus lactis, Lactobacillus leichmannii, Lactobacillus paracasei, Lactobacillus pentosus, Lactobacillus plantarum, Lactobacillus reuteri, Lactobacillus rhamnosus, Lactobacillus sakei* and *Lactobacillus salivarius.*

(4) The composition for maintaining and/or improving memory and learning ability according to (1) which is characterized in that the *Bifidobacterium* is one or more selected from *Bifidobacterium catenulatum, Bifidobacterium pseudolongum, Bifidobacterium bifidum, Bifidobacterium breve* and *Bifidobacterium longum.*

(5) The composition for maintaining and/or improving memory and learning ability according to (1) which is characterized in that the *Bifidobacterium* is not one or more selected from *Bifidobacterium adolescentis, Bifidobacterium animalis, Bifidobacterium catenulatum, Bifidobacterium pseudocatenulatum, Bifidobacterium bifidum, Bifidobacterium breve, Bifidobacterium pseudolongum, Bifidobacterium longum* and *Bifidobacterium longum* subspecies *infantis.*

(6) The composition for maintaining and/or improving memory and learning ability according to (1) which is characterized in that the *Streptococcus* is *Streptococcus thermophilus.*

(7) The composition for maintaining and/or improving memory and learning ability according to (1) which is characterized in that the *Streptococcus* is not one or more selected from *Streptococcus agalactiae, Streptococcus anginosus, Streptococcus iniae, Streptococcus intermedius, Streptococcus equi, Streptococcus oxalis, Streptococcus gallolyticus, Streptococcus gallolyticus* subspecies *gallolyticus, Streptococcus constellatus, Streptococcus gordonii, Streptococcus salivarius, Streptococcus sanguis, Streptococcus thermophilus, Streptococcus suis, Streptococcus zooepidemicus, Streptococcus sobrinus, Streptococcus pneumoniae, Streptococcus pyogenes, Streptococcus phage, Streptococcus faecalis, Streptococcus faecium, Streptococcus bovis, Streptococcus mitis* and *Streptococcus mutans.*

(8) The composition for maintaining and/or improving memory and learning ability according to (1) which is characterized in that the *Leuconostoc* is one or more selected from *Leuconostoc mesenteroides* subsp. *dextranicum* and *Leuconostoc lactis.*

(9) The composition for maintaining and/or improving memory and learning ability according to (1) which is characterized in that the *Leuconostoc* is not one or more selected from *Leuconostoc mesenteroides* subsp. *dextranicum, Leuconostoc mesenteroides* and *Leuconostoc lactis.*

(10) The composition for maintaining and/or improving memory and learning ability according to (1) which is characterized in that the *Pediococcus* is one or more selected from *Pediococcus acidilactici* and *Pediococcus pentosaceus.*

(11) The composition for maintaining and/or improving memory and learning ability according to (1) which is characterized in that the *Pediococcus* is not one or more selected from *Pediococcus acidilactici* and *Pediococcus pentosaceus.*

(12) The composition for maintaining and/or improving memory and learning ability according to (2) which is characterized in that the *Lactobacillus* is one or more selected from *Lactobacillus acidophilus* strain SBT1921, *Lactobacillus gasseri* strain SBT2056, *Lactobacillus gallinarum* strain SBT0316, *Lactobacillus johnsonii* strain SBT0307 and *Lactobacillus delbrueckii* subsp. *delbrueckii* strain SBT0413.

(13) The composition for maintaining and/or improving memory and learning ability according to (4) which is characterized in that the *Bifidobacterium* is one or more selected from *Bifidobacterium catenulatum* strain SBT11114, *Bifidobacterium pseudolongum* strain SBT2922, *Bifidobacterium bifidum* strain SBT10550, *Bifidobacterium breve* strain SBT10532 and *Bifidobacterium longum* strain SBT10527.

(14) The composition for maintaining and/or improving memory and learning ability according to (6) which is characterized in that the *Streptococcus* is *Streptococcus* thermophiles strain SBT0118.

(15) The composition for maintaining and/or improving memory and learning ability according to (8) which is characterized in that the *Leuconostoc* is one or more selected from *Leuconostoc mesenteroides* subsp. *dextranicum* strain SBT0096 and *Leuconostoc lactis* strain SBT2561.

(16) The composition for maintaining and/or improving memory and learning ability according to (10) which is characterized in that the *Pediococcus* is one or more selected from *Pediococcus acidilactici* strain SBT3331 and *Pediococcus pentosaceus* strain SBT2229.

(17) The composition for maintaining and/or improving memory and learning ability according to any of (1) to (16), wherein the maintenance and/or the improvement of memory and learning ability is prevention and/or improvement of decline, occurring with age (senescence), in memory and learning ability.

(18) The composition for maintaining and/or improving memory and learning ability according to (17), wherein the decline, occurring with age (senescence), in memory and learning ability does not include decline in memory and learning ability or decline in memory ability occurring with a brain disease, memory impairment and a psychiatric disorder.

(19) The composition for maintaining and/or improving memory and learning ability according to any of (1) to (18) which contains cells of the microorganism as an active ingredient instead of a peptide component contained in a culture supernatant of the microorganism.

(20) A food for maintaining and/or improving memory and learning ability, a medicine for maintaining and/or improving memory and learning ability or feed for maintaining and/or improving memory and learning ability which is characterized by containing the composition for maintaining and/or improving memory and learning ability according to any of (1) to (19).

(21) *Lactobacillus acidophilus* strain SBT1921 having an accession number of NITE P-02980, *Lactobacillus gallinarum* strain SBT0316 having an accession number of NITE P-02981, *Lactobacillus johnsonii* strain SBT0307 having an accession number of NITE P-02982, *Bifidobacterium catenulatum* strain SBT11114 having an accession number of NITE P-02983, *Bifidobacterium pseudolongum* strain SBT2922 having an accession number of NITE P-02984, *Bifidobacterium bifidum* strain SBT10550 having an accession number of NITE P-02985, *Bifidobacterium breve* strain SBT10532 having an accession number of NITE P-02986, *Bifidobacterium longum* strain SBT10527 having an accession number of NITE P-02987, *Streptococcus* thermophiles strain SBT0118 having an accession number of NITE P-02988, *Leuconostoc mesenteroides* subsp. *dextranicum* strain SBT0096 having an accession number of NITE P-02989, *Leuconostoc lactis* strain SBT2561 having an accession number of NITE P-02990, *Pediococcus acidilactici* strain SBT3331 having an accession number of NITE BP-02991 or *Pediococcus pentosaceus* strain SBT2229 having an accession number of NITE BP-02992.

Advantageous Effects of Invention

According to the invention, decline in memory and learning ability occurring with age (senescence) can be prevented and/or improved. The invention is effective for improving the quality of life in daily lives of elderly people who are concerned about their decline in memory and learning ability.

BRIEF DESCRIPTION OF DRAWINGS

FIG. 1 A figure illustrating the summary of a thermotaxis test using *C. elegans*.

FIG. 2 A figure showing the change in the memory index with age of *C. elegans* and the memory indexes of aged adult worms which have taken lactic acid bacteria.

DESCRIPTION OF EMBODIMENTS

The "maintenance and/or improvement of memory and learning ability" in the present specification preferably means prevention and/or improvement of decline, occurring with age (senescence), in memory and learning ability and more preferably means prevention and/or improvement of decline, occurring with age (senescence), in memory ability. Furthermore, the "decline, occurring with age (senescence), in memory and learning ability" or the "decline, occurring with age (senescence), in memory ability" in the present specification preferably does not include decline in memory and learning ability or decline in memory ability occurring with dementia such as Alzheimer's disease and Huntington's disease, a brain disease including basal ganglia disease such as Parkinson's disease, memory impairment such as amnesia, memory loss and Korsakoff syndrome and a psychiatric disorder such as major depressive disorder, anxiety disorder, bipolar disorder, schizophrenia, dyssomnia and stress disorder.

The "composition" in the present specification preferably means a pharmaceutical composition or a food composition.

The composition for maintaining and/or improving memory and learning ability of the invention is characterized by containing any of the microorganisms belonging to *Lactobacillus, Bifidobacterium, Streptococcus, Leuconostoc* and *Pediococcus* as an active ingredient. The microorganisms belonging to *Lactobacillus, Bifidobacterium, Streptococcus, Leuconostoc* and *Pediococcus* are preferably species *Lactobacillus acidophilus*, species *Lactobacillus gasseri*, species *Lactobacillus gallinarum*, species *Lactobacillus johnsonii, Lactobacillus delbrueckii* subsp. *delbrueckii*, species *Bifidobacterium catenulatum*, species *Bifidobacterium pseudolongum*, species *Bifidobacterium bifidum*, species *Bifidobacterium breve*, species *Bifidobacterium longum*, species *Streptococcus thermophilus, Leuconostoc mesenteroides* subsp. *dextranicum*, species *Leuconostoc lactis*, species *Pediococcus acidilactici* and *Pediococcus pentosaceus. Lactobacillus acidophilus* strain SBT1921, *Lactobacillus gasseri* strain SBT2056, *Lactobacillus gallinarum* strain SBT0316, *Lactobacillus johnsonii* strain SBT0307, *Lactobacillus delbrueckii* subsp. *delbrueckii* strain SBT0413, *Bifidobacterium catenulatum* strain SBT11114, *Bifidobacterium pseudolongum* strain SBT2922, *Bifidobacterium bifidum* strain SBT10550, *Bifidobacterium breve* strain SBT10532, *Bifidobacterium longum* strain SBT10527, *Streptococcus thermophilus* strain SBT0118, *Leuconostoc mesenteroides* subsp. *dextranicum* strain SBT0096, *Leuconostoc lactis* strain SBT2561, *Pediococcus acidilactici* strain SBT3331 and *Pediococcus pentosaceus* strain SBT2229 are further preferable, but the microorganisms are not particularly limited as long as the microorganisms are those belonging to *Lactobacillus, Bifidobacterium, Streptococcus, Leuconostoc* or *Pediococcus* having the effect of maintaining and/or improving memory and learning ability of the invention.

The microorganisms belonging to *Lactobacillus, Bifidobacterium, Streptococcus, Leuconostoc* or *Pediococcus* can be used alone or may be appropriately used in combination with two or more lactic acid bacteria. Moreover, the microorganisms belonging to *Lactobacillus, Bifidobacterium, Streptococcus, Leuconostoc* or *Pediococcus* can be cultured according to a general method for culturing lactic acid bacteria. For the culture medium, various media such as a milk medium, a medium containing a milk component and a semisynthetic medium which does not contain the same can be used. Examples of such media include a reduced skim milk medium, MRS medium and the like.

Bacterial cells isolated from the obtained culture by cell collection means such as centrifugation can be directly used as an active ingredient of the invention. Bacterial cells after concentration, drying, lyophilization or the like can also be used, and dead cells obtained by heat drying or the like may also be used. As the bacterial cells, not only those which are purely isolated but also a culture, a suspension, another bacterial cell-containing product and a cytoplasm or cell wall fraction obtained by treating bacterial cells with an enzyme or physical means can also be used. Examples of the form of the culture or the like include not only a culture using a medium that is generally used for culturing lactic acid bacteria such as MRS medium (manufactured by DIFCO), which is a synthetic medium, and a reduced skim milk medium but also dairy products such as cheese, fermented milk and dairy product lactic acid bacteria beverage and the like, although the form is not particularly limited.

For the formulation of the agent for maintaining and/or improving memory and learning ability of the invention, concentration or lyophilization may be conducted after appropriately mixing an excipient, a stabilizer, a corrigent and the like which are acceptable for formulation, or dead cells may be obtained by heat drying. These dried product, concentrate and paste are also included. Moreover, within the range of not impairing the effect of maintaining and/or improving memory and learning ability of the bacterial cells or the culture of the microorganism belonging to *Lactobacillus, Bifidobacterium, Streptococcus, Leuconostoc* or *Pediococcus*, an excipient, a binder, a disintegrating agent, a lubricant, a flavoring agent, a suspending agent, a coating agent or any other drugs may be mixed for formulation. As the dosage form, tablets, capsules, granules, powder, dusting powder, syrup and the like are acceptable, and such a dosage form is desirably orally administered.

The composition for maintaining and/or improving memory and learning ability of the invention may be blended in any food or drink and may be added to a raw material during the production process of a food or a drink. Examples of the food or the drink include dairy products such as cheeses, fermented milk, dairy product lactic acid bacteria beverages, lactic acid bacteria beverages, butter and margarine, beverages such as milk beverages, fruit juices and soft drinks, processed egg products such as jellies, candies, pudding and mayonnaise, confectionaries-breads such as butter cakes, various kinds of powder milk, baby foods, nutritional compositions and the like, although the food or the drink is not particularly limited. Furthermore, the composition for maintaining and/or improving memory and learning ability of the invention can be blended in feed. Similar to the food or the drink, the composition may be blended in any feed and may be added to a raw material during the production process of feed.

When cells or a culture of the microorganism belonging to *Lactobacillus, Bifidobacterium, Streptococcus, Leuconostoc* or *Pediococcus* is used by blending in a material or in a processed product of the material such as a composition for maintaining and/or improving memory and learning ability or a food or a drink, a nutritional composition, feed or the like for maintaining and/or improving memory and learning ability, the proportion of the cells or the culture of the microorganism belonging to *Lactobacillus, Bifidobacterium, Streptococcus, Leuconostoc* or *Pediococcus* is not particularly limited and may be appropriately adjusted according to the easiness of production or a preferable daily dosage. Although the proportion is individually decided considering the symptom, the age and the like of the subject of the administration, in the case of a general adult, for example, the blended amount or the like may be adjusted in such a manner that 10 to 200 g of a culture or the like of *Lactobacillus gasseri* or 0.1 to 5,000 mg of bacterial cells thereof themselves can be taken. Through intake in this manner, a desired effect can be exhibited.

As a screening method for lactic acid bacteria which prevent and/or improve decline, occurring with age (senescence), in memory and learning ability in the invention, a thermotaxis test using *C. elegans* was conducted. In general, when physiological functions of food components and drugs are examined, a higher animal such as mouse, rat, dog and monkey is used. However, the use requires a lot of labor, time and costs, and sufficient care should be taken for the ethical aspects. As an alternative method for animal research, tests using culture cells isolated from animal tissues and the like have been also conducted.

*C. elegans* is a nonparasitic multicellular organism living in soil and is widely used as a model organism in various research fields in view of the easy handling as a laboratory animal and because the cell lineages of about 1000 somatic cells constituting the body have been all elucidated and also because *C. elegans* has a nervous system. In particular, *C. elegans* has contributed a lot in various research fields of cell death, nerves, development, aging and the like. In recent years, medicines and food components which are effective for preventing or improving various neurodegenerative diseases such as Alzheimer's disease, amyotrophic lateral sclerosis (ALS), Parkinson's disease and Huntington's disease have been searched using *C. elegans*, which is a model for the neurodegenerative diseases.

It is known that *C. elegans* has a simple neural circuit but memorizes-learns the presence or absence of diet in association with information of the salt concentration, the temperature and the like in the environment the *C. elegans* is placed. Thus, *C. elegans* can be used as a model system for assessing cognitive function such as associative learning and memory (Nature, 376, 344-348 (1995)).

The invention is explained below in further detail based on Examples, but the invention is not construed as being limited to the Examples.

[Test Example 1] Assessment of Lactic Acid Bacteria Preventing and/or Improving Decline Occurring with Age (Senescence) in Cognitive Function As the *C. elegans* used in the present specification, strain N2, which is the wild type, was used and cultured according to "Laboratory Manual for Nematode". 1. Test Method (1) Bacteria to be Tested The bacterial strains shown in Table 1 were subjected to screening.

TABLE 1

Bacteria to be Tested

| Bacteria Species | Bacteria Strain | Accession Number Given by Depositary (Receipt Number) |
|---|---|---|
| *Lactobacillus acidophilus* | SBT1921 | NITE P-02980 |
| *Lactobacillus gasseri* | SBT2056 | FERM P-11038 |
| *Lactobacillus gallinarum* | SBT0316 | NITE P-02981 |
| *Lactobacillus johnsonii* | SBT0307 | NITE P-02982 |
| *Lactobacillus delbruekii* subsp. *delbruekii* | SBT0413 | NITE P-02642 |
| *Bifidobacterium catenulatum* | SBT11114 | NITE P-02983 |
| *Bifidobacterium pseudolongum* | SBT2922 | NITE P-02984 |
| *Bifidobacterium bifidum* | SBT10550 | NITE P-02985 |
| *Bifidobacterium breve* | SBT10532 | NITE P-02986 |
| *Bifidobacterium longum* | SBT10527 | NITE P-02987 |
| *Streptococcus thermophilus* | SBT0118 | NITE P-02988 |
| *Leuconostoc mesenteroides* subsp. *dextranicum* | SBT0096 | NITE P-02989 |
| *Leuconostoc lactis* | SBT2561 | NITE P-02990 |
| *Pediococcus acidilactici* | SBT3331 | NITE P-02991 (NITE ABP-02991) |
| *Pediococcus pentosaceus* | SBT2229 | NITE P-02992 (NITE ABP-02992) |

(2) Test Procedures (i) Preparation of Assessment Samples

The bacteria to be tested in (1) above were cultured under the conditions in Table 2. The cultured bacterial cells were centrifuged (7,000×g, 4° C., 15 minutes), and the supernatants were disposed of. After washing the bacterial cells with physiological saline, the wet weights of the bacterial cells were measured. The bacterial cells were suspended again in NG buffer (0.3% NaCl, 1 mM $CaCl_2$, 1 mM $MgSO_4$, 25 mM phosphate buffer [pH6.0]) to a concentration of 0.05 g/ml, and the suspensions each in a volume of 200 μl were spread on *C. elegans*-culturing plates (NGM plates) to obtain sample plates. As a control, *Escherichia coli* strain OP50, which is generally used as food of *C. elegans*, was used.

TABLE 2

Culture Conditions for Culturing Bacteria to be Tested

| Genus | Medium | Culture Temperature | Culture Period |
|---|---|---|---|
| *Lactobacillus* | MRS medium (manufactured by Difco) | 37° C. | 16 h |
| *Bifidobacterium* | GAM medium (manufactured by Nissui Pharmaceutical Co., Ltd.) plus 1% glucose (manufactured by FUJIFILM Wako Pure Chemical Corporation) | 37° C. | 16 h |
| *Streptococcus* | MRS medium (manufactured by Difco) | 37° C. | 16 h |
| *Leuconostoc* | MRS medium (manufactured by Difco) | 30° C. | 16 h |
| *Pediococcus* | MRS medium (manufactured by Difco) | 37° C. | 16 h |

(ii) Preparation of Aged Worms which have Taken Lactic Acid Bacteria

Eggs of *C. elegans* collected by bleaching treatment were spread on plates on which OP50 had been spread and left still at 23° C. for three days, and young adult worms were thus obtained. The adult worms were collected with NG buffer, moved to a plate on which a lactic acid bacterium had been spread or a plate on which OP50 had been spread and cultured at 23° C. for four days, and aged worms were thus obtained.

(iii) Screening by Thermotaxis Test

The thermotaxis test was conducted as follows according to the method described by Ito H. et al. (J. Neurosci. Methods, 154, 45-52 (2006)). Two thermostat baths were prepared. By immersing one leg of a U-shaped aluminum stand (21.5 cm×60 cm×1.5 cm thickness) in the thermostat bath at a low temperature (5° C.) and immersing the other leg in the thermostat bath at a high temperature (35° C.), a linear temperature gradient of about 5° C. to 35° C. was created on the aluminum stand. An agar plate in a square dish was placed on the aluminum stand in such a manner that the point at 20° C. would come to the middle. The young adult worms or the aged adult worms were released in the middle of the plate, and the distribution of *C. elegans* in the temperature gradient after an hour was assessed. Regarding the memory and learning ability, the plate was equally divided into eight sections in the direction of the temperature gradient, and the percentage of *C. elegans* in the two sections around the cultivation temperature (23° C.) was assessed as the memory index (FIG. 1). Moreover, by the Dunnett's multiple test, the presence or absence of a significant difference was assessed using the aged adult worms which had taken OP50 as a control (it was determined that there was a significant difference when $p<0.05$).

2. Test Results

The results of screening are shown in FIG. 2. The memory index of the aged worms decreased as compared to that of the young adult worms.

The memory indexes of the aged worms which had taken *Lactobacillus acidophilus* strain SBT1921, *Lactobacillus gasseri* strain SBT2056, *Lactobacillus gallinarum* strain SBT0316, *Lactobacillus johnsonii* strain SBT0307, *Lactobacillus delbrueckii* subsp. *delbrueckii* strain SBT0413, *Bifidobacterium catenulatum* strain SBT11114, *Bifidobacterium pseudolongum* strain SBT2922, *Bifidobacterium bifidum* strain SBT10550, *Bifidobacterium breve* strain SBT10532, *Bifidobacterium longum* strain SBT10527, *Streptococcus thermophilus* strain SBT0118, *Leuconostoc mesenteroides* subsp. *dextranicum* strain SBT0096, *Leuconostoc lactis* strain SBT2561, *Pediococcus acidilactici* strain SBT3331 and *Pediococcus pentosaceus* strain SBT2229 increased significantly as compared to the memory index of those which had taken OP50. That is, it was found that intake of the bacterial cells can prevent and/or improve decline, occurring with age (senescence), in memory and learning ability.

(Example 1) Production of Agent for Maintaining and/or Improving Memory and Learning Ability (Granules)

*Lactobacillus gallinarum* strain SBT0316 was inoculated into 5% by weight in an edible synthetic medium (containing 0.5% yeast extract and 0.1% trypticase peptone) and cultured at 38° C. for 15 hours, and then the bacterial cells were collected by centrifugation. The collected bacterial cells were lyophilized, and lyophilized powder of the bacterial cells was thus obtained. One gram of the lyophilized powder was mixed with 5 g of lactose, and the mixture was formed into granules to obtain an agent for maintaining and/or improving memory and learning ability of the invention.

(Example 2) Production of Agent for Maintaining and/or Improving Memory and Learning Ability (Powder)

In accordance with the provisions of the 13th revised Japanese Pharmacopoeia Guideline General Formulation "Powder", 400 g of lactose (The Japanese Pharmacopoeia) and 600 g of potato starch (The Japanese Pharmacopoeia) were added to 10 g of the lyophilized powder of *Lactobacillus gallinarum* strain SBT0316 obtained in Example 1 and uniformly mixed, and an agent for maintaining and/or improving memory and learning ability of the invention was thus produced.

(Example 3) Production of Nutritional Composition for Maintaining and/or Improving Memory and Learning Ability

*Lactobacillus gallinarum* strain SBT0316 was inoculated into 5% by weight in an edible synthetic medium (containing 0.5% yeast extract and 0.1% trypticase peptone) and cultured at 38° C. for 15 hours. Then, the bacterial cells were collected by centrifugation, and the collected bacterial cells were lyophilized. To 40 g of vitamin C or 40 g of a mixture containing same amounts of vitamin C and citric acid, 100 g of granulated sugar and 60 g of a mixture containing same amounts of corn starch and lactose, 40 g of the lyophilized powder of the lyophilized powder was added and mixed. The mixture was packed in bags, and a nutritional composition for maintaining and/or improving memory and learning ability of the invention was thus produced.

(Example 4) Production of Drink for Maintaining and/or Improving Memory and Learning Ability After dissolving 1 g of the *Lactobacillus gallinarum* strain SBT0316 obtained in Example 3 in 699 g of deionized water, the mixture was heated to 40° C. and then stirred and mixed using an ultradisperser (ULTRA-TURRAX T-25; manufactured by IKA Japan K.K.) at 9,500 rpm for 20 minutes. After adding 100 g of maltitol, 2 g of an acidulant, 20 g of reduced starch syrup, 2 g of a flavor and 176 g of deionized water, 100-ml glass bottles were filled with the mixture, sterilized at 95° C. for 15 seconds and then tightly stoppered. Ten bottles (100 ml) of a drink for maintaining and/or improving memory and learning ability of the invention were thus produced.

(Example 5) Production of Feed for Maintaining and/or Improving Memory and Learning Ability Twelve kilograms of a soybean meal, 14 kg of powdered skim milk, 4 kg of soybean oil, 2 kg of corn oil, 23.2 kg of palm oil, 14 kg of corn starch, 9 kg of flour, 2 kg of wheat bran, 5 kg of a vitamin mixture, 2.8 kg of cellulose and 2 kg of a mineral mixture were blended and sterilized at 120° C. for four minutes. Then, 10 kg of the *Lactobacillus gallinarum* strain SBT0316 obtained in Example 3 was blended. Feed for maintaining and/or improving memory and learning ability of the invention was thus produced.

(Example 6) Production of Fermented Milk for Maintaining and/or Improving Memory and Learning Ability

*Lactobacillus gallinarum* strain SBT0316 was inoculated into 5% by weight in an edible synthetic medium (0.5% yeast extract, 0.1% trypticase peptone added) and cultured at 37° C. for 17 hours, and then, the bacterial cells were collected by centrifugation and lyophilized. Five grams of the lyophilized bacterial cells, 1700 g of powdered skim milk, 300 g of glucose and 7695 g of deionized water were mixed and sterilized with heat by keeping the mixture at 95°

C. for two hours. The resultant was cooled to 37° C., and 300 g of a lactic acid bacterium starter (Lb. *casei*) was inoculated. After stirring and mixing, the mixture was fermented in an incubator kept at 37° C. until the pH reached 4.0. After the pH reached 4.0, the resultant was cooled to 10° C. or lower, and 10 kg of fermented milk for maintaining and/or improving memory and learning ability of the invention was thus produced.

ACCESSION NUMBER (1) *Lactobacillus acidophilus* strain SBT1921 (accession number: NITE P-02980, date of accession: Jun. 26, 2019), depositary: 2-5-8 Kazusakamatari, Kisarazu-shi, Chiba 2920818, Japan, NITE Patent Microorganisms Depositary (NPMD), National Institute of Technology and Evaluation (2) *Lactobacillus gallinarum* strain SBT0316 (accession number: NITE P-02981, date of accession: Jun. 26, 2019), depositary: 2-5-8 Kazusakamatari, Kisarazu-shi, Chiba 2920818, Japan, NITE Patent Microorganisms Depositary (NPMD), National Institute of Technology and Evaluation (3) *Lactobacillus johnsonii* strain SBT0307 (accession number: NITE P-02982, date of accession: Jun. 26, 2019), depositary: 2-5-8 Kazusakamatari, Kisarazu-shi, Chiba 2920818, Japan, NITE Patent Microorganisms Depositary (NPMD), National Institute of Technology and Evaluation (4) *Bifidobacterium catenulatum* strain SBT11114 (accession number: NITE P-02983, date of accession: Jun. 26, 2019), depositary: 2-5-8 Kazusakamatari, Kisarazu-shi, Chiba 2920818, Japan, NITE Patent Microorganisms Depositary (NPMD), National Institute of Technology and Evaluation (5) *Bifidobacterium pseudolongum* strain SBT2922 (accession number: NITE P-02984, date of accession: Jun. 26, 2019), depositary: 2-5-8 Kazusakamatari, Kisarazu-shi, Chiba 2920818, Japan, NITE Patent Microorganisms Depositary (NPMD), National Institute of Technology and Evaluation (6) *Bifidobacterium bifidum* strain SBT10550 (accession number: NITE P-02985, date of accession: Jun. 26, 2019), depositary: 2-5-8 Kazusakamatari, Kisarazu-shi, Chiba 2920818, Japan, NITE Patent Microorganisms Depositary (NPMD), National Institute of Technology and Evaluation (7) *Bifidobacterium breve* strain SBT10532 (accession number: NITE P-02986, date of accession: Jun. 26, 2019), depositary: 2-5-8 Kazusakamatari, Kisarazu-shi, Chiba 2920818, Japan, NITE Patent Microorganisms Depositary (NPMD), National Institute of Technology and Evaluation (8) *Bifidobacterium longum* strain SBT10527 (accession number: NITE P-02987, date of accession: Jun. 26, 2019), depositary: 2-5-8 Kazusakamatari, Kisarazu-shi, Chiba 2920818, Japan, NITE Patent Microorganisms Depositary (NPMD), National Institute of Technology and Evaluation (9) *Streptococcus thermophilus* strain SBT0118 (accession number: NITE P-02988, date of accession: Jun. 26, 2019), depositary: 2-5-8 Kazusakamatari, Kisarazu-shi, Chiba 2920818, Japan, NITE Patent Microorganisms Depositary (NPMD), National Institute of Technology and Evaluation

(10) *Leuconostoc mesenteroides* subsp. *dextranicum* strain SBT0096 (accession number: NITE P-02989, date of accession: Jun. 26, 2019), depositary: 2-5-8 Kazusakamatari, Kisarazu-shi, Chiba 2920818, Japan, NITE Patent Microorganisms Depositary (NPMD), National Institute of Technology and Evaluation

(11) *Leuconostoc lactis* strain SBT2561 (accession number: NITE P-02990, date of accession: Jun. 26, 2019), depositary: 2-5-8 Kazusakamatari, Kisarazu-shi, Chiba 2920818, Japan, NITE Patent Microorganisms Depositary (NPMD), National Institute of Technology and Evaluation

(12) *Pediococcus acidilactici* strain SBT3331 (receipt number: NITE ABP-02991, date of receipt: Jul. 13, 2020, date of original accession: Jun. 26, 2019), depositary: 2-5-8 Kazusakamatari, Kisarazu-shi, Chiba 2920818, Japan, NITE Patent Microorganisms Depositary (NPMD), National Institute of Technology and Evaluation

(13) *Pediococcus pentosaceus* strain SBT2229 (receipt number: NITE ABP-02992, date of receipt: Jul. 13, 2020, date of original accession: Jun. 26, 2019), depositary: 2-5-8 Kazusakamatari, Kisarazu-shi, Chiba 2920818, Japan, NITE Patent Microorganisms Depositary (NPMD), National Institute of Technology and Evaluation

(14) *Lactobacillus* gasseri strain SBT2056 (receipt number: NITE: BP-11038, date of receipt Oct. 9, 2008, date of original accession: Apr. 22, 1986), depositary: Tsubuka Central 6, 1-1 Higashi 1-chome, Tsukuba-shi, Ibaraki-ken, 305-8566, Japan, National Institute of Advanced Industrial Science and Technology (AIST)

(15) *Lactobacillus delbrueckii* subsp. *delbrueckii* strain SBT0413 (receipt number: NITE: BP-02642, date of receipt May 27, 2019, date of original accession: Feb. 21, 2018) depositary: 2-5-8 Kazusakamatari, Kisarazu-shi, Chiba 2920818, Japan, NITE Patent Microorganisms Depositary (NPMD), National Institute of Technology and Evaluation

The invention claimed is:

1. A method for maintaining and/or improving memory and learning ability comprising administering a composition containing cells or a culture of *Lactobacillus gasseri* to a human subject aged 65 or more in need of improving a decline, occurring with age (senescence), in memory and learning ability, or (ii) a decline, occurring with age (senescence), in memory, wherein (i) the decline, occurring with age (senescence), in memory and learning ability and (ii) the decline, occurring with age (senescence), in memory does not include a decline in memory and learning ability or decline in memory occurring with Alzheimer's disease, Huntington's disease, Parkinson's disease, amnesia, Korsakoff syndrome, major depressive disorder, anxiety disorder, bipolar disorder, schizophrenia, dyssomnia and stress disorder.

2. The method for maintaining and/or improving memory and learning ability according to claim 1, wherein the *Lactobacillus gasseri* is *Lactobacillus gasseri* strain SBT2056 (FERM BP-11038).

3. A method for maintaining and/or improving memory and learning ability, comprising administering a food for maintaining and/or improving memory and learning ability, a medicine for maintaining and/or improving memory and learning ability, or feed for maintaining and/or improving memory and learning ability, to a human subject aged 65 or more in need of improving (i) a decline, occurring with age (senescence), in memory and learning ability, or (ii) a decline, occurring with age (senescence), in memory, wherein the food, medicine, or feed comprises cells or a culture of s *Lactobacillus gasseri*, and wherein (i) the decline, occurring with age (senescence), in memory and learning ability and (ii) the decline, occurring with age (senescence), in memory does not include a decline in memory and learning ability or decline in memory occurring with Alzheimer's disease, Huntington's disease, Parkinson's disease, amnesia, Korsakoff syndrome, major depressive disorder, anxiety disorder, bipolar disorder, schizophrenia, dyssomnia and stress disorder.

4. The method for maintaining and/or improving memory and learning ability according to claim 3, wherein the *Lactobacillus gasseri* strain SBT2056 (FERM BP-11038).

5. A method for maintaining and/or improving memory and learning ability comprising administering cells consisting of *Lactobacillus gasseri* to a human subject aged 65 or more in need of improving (i) a decline, occurring with age (senescence), in memory and learning ability, or (ii) a decline, occurring with age (senescence), in memory, wherein (i) the decline, occurring with age (senescence), in memory and learning ability and (ii) the decline, occurring with age (senescence), in memory does not include a decline in memory and learning ability or decline in memory occurring with Alzheimer's disease, Huntington's disease, Parkinson's disease, amnesia, Korsakoff syndrome, major depressive disorder, anxiety disorder, bipolar disorder, schizophrenia, dyssomnia and stress disorder.

6. A method for maintaining and/or improving memory and learning ability comprising administering a composition consisting of cells of *Lactobacillus gasseri* and at least one selected from the group consisting of an excipient, a binder, a disintegrating agent, a lubricant, a flavoring agent, a suspending agent, and a coating agent to a human subject aged 65 or more in need of improving (i) a decline, occurring with age (senescence), in memory and learning ability, or (ii) a decline, occurring with age (senescence), in memory, wherein (i) the decline, occurring with age (senescence), in memory and learning ability and (ii) the decline, occurring with age (senescence), in memory does not include a decline in memory and learning ability or decline in memory occurring with Alzheimer's disease, Huntington's disease, Parkinson's disease, amnesia, Korsakoff syndrome, major depressive disorder, anxiety disorder, bipolar disorder, schizophrenia, dyssomnia and stress disorder.

7. The method for maintaining and/or improving memory and learning ability according to claim 5, wherein the *Lactobacillus gasseri* is *Lactobacillus gasseri* strain SBT2056 (FERM BP-11038).

8. The method for maintaining and/or improving memory and learning ability according to claim 6, wherein the *Lactobacillus gasseri* is *Lactobacillus gasseri* strain SBT2056 (FERM BP-11038).

* * * * *